United States Patent [19]
Thompson

[11] Patent Number: 5,980,450
[45] Date of Patent: Nov. 9, 1999

[54] COUPLING DEVICE FOR USE IN AN IMAGING SYSTEM

[75] Inventor: Robert Lee Thompson, Rogers, Ark.

[73] Assignee: Pinotage, LLC, Rogers, Ark.

[21] Appl. No.: 09/064,452

[22] Filed: Apr. 22, 1998

Related U.S. Application Data

[60] Provisional application No. 60/045,817, May 7, 1997.

[51] Int. Cl.$^6$ ..................................................... A61B 1/04
[52] U.S. Cl. ........................... 600/112; 600/122; 600/167
[58] Field of Search ................................. 600/112, 122, 600/124, 133, 167, 109

[56] References Cited

U.S. PATENT DOCUMENTS

| | | |
|---|---|---|
| Re. 34,110 | 10/1992 | Opie et al. . |
| 4,646,722 | 3/1987 | Silverstein et al. . |
| 4,736,733 | 4/1988 | Adair . |
| 4,741,326 | 5/1988 | Sidall et al. . |
| 4,878,113 | 10/1989 | Nakamura . |
| 4,914,521 | 4/1990 | Adair . |
| 4,947,827 | 8/1990 | Opie et al. . |
| 4,947,829 | 8/1990 | Bullard . |
| 5,131,380 | 7/1992 | Heller et al. . |
| 5,168,863 | 12/1992 | Kurtzer . |
| 5,188,093 | 2/1993 | Lafferty et al. ........................ 600/109 |
| 5,237,984 | 8/1993 | Williams, III et al. . |
| 5,239,981 | 8/1993 | Anapliotis . |
| 5,301,657 | 4/1994 | Lafferty et al. . |
| 5,334,150 | 8/1994 | Kaali . |
| 5,337,734 | 8/1994 | Saab . |
| 5,402,768 | 4/1995 | Adair . |
| 5,406,939 | 4/1995 | Bala . |
| 5,408,992 | 4/1995 | Hamlin et al. . |
| 5,431,150 | 7/1995 | Yabe et al. . |
| 5,447,148 | 9/1995 | Oneda et al. . |
| 5,531,664 | 7/1996 | Adachi et al. . |
| 5,591,119 | 1/1997 | Adair ..................................... 600/122 |
| 5,591,192 | 1/1997 | Privitera et al. . |
| 5,643,175 | 7/1997 | Adair . |
| 5,792,045 | 8/1998 | Adair ..................................... 600/122 |
| 5,876,328 | 3/1999 | Fox et al. ............................... 600/122 |

FOREIGN PATENT DOCUMENTS

| | | |
|---|---|---|
| 0 570 161 | 11/1993 | European Pat. Off. . |
| 89 14 215 | 2/1991 | Germany . |
| 2 148 526 | 5/1985 | United Kingdom . |

*Primary Examiner*—John P. Leubecker
*Attorney, Agent, or Firm*—Wolf, Greenfield & Sacks, P.C.

[57] ABSTRACT

According to one embodiment, an apparatus for mating a first instrument having an image sensor to a second instrument includes: a coupler having first and second ends respectively adapted to mate with the first and second instruments; a sheath, mounted to the coupler, that is extendable to accommodate at least one portion of the first instrument when the first instrument is mated with the first end of the coupler; and a focusing mechanism to focus light onto the image sensor, the focusing mechanism being uncovered by the sheath when the first end of the coupling device is mated with the first instrument and the sheath is extended to accommodate the at least one portion of the first instrument. According to another embodiment, an apparatus for mating with an imaging-producing scope includes: an imaging unit including an image sensor and a lens; and a coupler having first and second ends, the first end being adapted to mate with the imaging unit and the second end being adapted to mate with the scope. According to another embodiment, a method for mating a sterile instrument with a non-sterile instrument while maintaining a sterile barrier therebetween includes the steps of: (a) using a sterile coupling device having a sterile sheath attached thereto to mate the sterile instrument with the non-sterile instrument by mating a first portion of the sterile coupling device with the sterile instrument and a second portion of the sterile coupling device with the non-sterile instrument; and (b) extending the sterile sheath to at least partially accommodate the non-sterile instrument.

28 Claims, 4 Drawing Sheets

COUPLING DEVICE FOR USE IN AN IMAGING SYSTEM

This application claims the benefit of U.S. Provisional Application Ser. No. 60/045,817, filed May 7, 1997.

BACKGROUND OF THE INVENTION

1. Field of the Invention

The present invention is directed to a method and apparatus for coupling together a scope and an imaging device, as well as a system resulting therefrom.

2. Discussion of Related Art

An endoscope is a device, commonly used in the medical field, that may be used to view an interior cavity of a body. An endoscope typically includes an elongated shaft having a distal end to be inserted into a patient, and a proximal end having an eyepiece through which a user, such as a physician, may view the interior of the body cavity.

For some medical procedures, it is desirable to present an image of the interior of the body cavity on a display of an imaging system. For this purpose, it is known to use a coupling device to couple the eyepiece of an endoscope to an electronic image sensor of an imaging system so that the image sensor can sense the image produced by the endoscope and transmit an electronic signal representing the image to the imaging system display. The endoscope is typically sterilized prior to insertion into the patient. In addition, some technique is typically employed to ensure that the imaging system and the device for coupling it to the endoscope do not compromise the sterile environment.

FIG. 1 shows an example of such a prior art viewing system that includes four primary components: an endoscope 16 for insertion into the patient, an imaging unit 6 (connected to a monitor 46) for displaying an image within the patient's body cavity on the monitor, a coupling device 8 for coupling together the endoscope 16 and the imaging unit 6 and a sterile condom-like sheath 5 which prevents the coupling device 8 and the imaging unit 6 from contaminating the sterile environment.

Endoscope 16 includes a distal end 13 which is adapted to be inserted into the patient (not shown) to view an object 9 within a body cavity of the patient. At its proximal end, the endoscope 16 includes an eyepiece 36 at which an image of the object 9 is presented. Imaging unit 6 includes housing 15 which houses an image sensor 14. The image sensor 14 senses an image along an imaging axis 17, and converts the sensed image into an electrical signal. This signal is passed, via a cable 26, to a monitor or display 46 which presents the sensed image to a user.

Coupling device 8 is used to couple together the eyepiece 36 of endoscope 16 and the housing 15, so that the imaging axis 17 of image sensor 14 passes through the eyepiece 36 and the length of the endoscope 16. In this manner, the image sensor 14 can sense the image of the object 9 within the patient. Coupling device 8 includes a lens 20 which is movably mounted therein and a focusing mechanism 11 which may be manipulated to adjust a position of lens 20 within coupling device 8. When the coupling device 8 is mounted to the housing 15, lens 20 is aligned with the optical axis 17 of the image sensor 14 so that the optical axis 17 passes through the lens 20. By manipulating focusing mechanism 11, the focal length between the lens 20 and the image sensor 14 may be adjusted to focus the image (e.g., of object 9) that is presented at the eyepiece 36 on the image sensor 14.

The coupling device 8 and the housing 15 of the imaging unit 6 are typically not sterile. Therefore, the condom-like sheath 5 is disposed between the eyepiece 36 and the coupling device 8 to prevent the non-sterile components from contaminating the sterile endoscope 16. Typically, the sheath 5 is primarily formed from a flexible material that is not optically pure, and that would not convey a clear image from the eyepiece 36 to the image sensor 14. Thus, a window 7 of more optically pure material is typically provided in the sheath 5. When the system is in use, the window 7 is aligned between the eyepiece 36 and the coupling device 8 so that the optical axis 17 of the image sensor 14 passes through the window 7.

SUMMARY OF THE INVENTION

According to one aspect of the present invention, an apparatus for mating an image-producing scope with an imaging instrument includes: a coupler having a first end adapted to mate with the image-producing scope and a second end adapted to mate with the imaging instrument; and a sterile sheath which is attached to the coupler without intercepting the optical axis.

According to another aspect of the invention, an apparatus for mating a first instrument having an image sensor to a second instrument includes: a coupler having first and second ends respectively adapted to mate with the first and second instruments; a sheath, mounted to the coupler, that is extendable to accommodate at least one portion of the first instrument when the first instrument is mated with the first end of the coupler; and a focusing mechanism to focus light onto the image sensor, the focusing mechanism being uncovered by the sheath when the first end of the coupling device is mated with the first instrument and the sheath is extended to accommodate the at least one portion of the first instrument.

According to yet another aspect, an apparatus for mating with an imaging-producing scope includes: an imaging unit including an image sensor and a lens; and a coupler having first and second ends, the first end being adapted to mate with the imaging unit and the second end being adapted to mate with the scope.

According to another aspect of the present invention, an apparatus for mating a scope with an imaging instrument includes: a coupler having first and second ends, the first end being adapted to mate with the scope, the second end being adapted to mate with the imaging instrument, the coupler defining a light-transmissive passage between the first and second ends so that the image produced by the scope can be transmitted through the light-transmissive passage to the imaging sensor, the light-transmissive passage being free of a refractive lens that intercepts the optical axis.

According to another aspect of the present invention, a method for mating a sterile instrument with a non-sterile instrument while maintaining a sterile barrier therebetween includes the steps of: (a) using a sterile coupling device having a sterile sheath attached thereto to mate the sterile instrument with the non-sterile instrument by mating a first portion of the sterile coupling device with the sterile instrument and a second portion of the sterile coupling device with the non-sterile instrument; and (b) extending the sterile sheath to at least partially accommodate the non-sterile instrument.

According to another aspect of the invention, a coupler for coupling a scope with an imaging instrument includes: a body having a first end adapted to mate with the scope and a second end adapted to mate with the imaging instrument; and a sheath that is hermetically sealed to the coupler.

According to yet another aspect, a coupler for coupling a scope with an imaging instrument includes: a body having a first end adapted to mate with the scope and a second end adapted to mate with the imaging instrument; and a focusing mechanism adapted to focus a refractive lens within the imaging instrument.

DETAILED DESCRIPTION OF THE INVENTION

Figure 1:
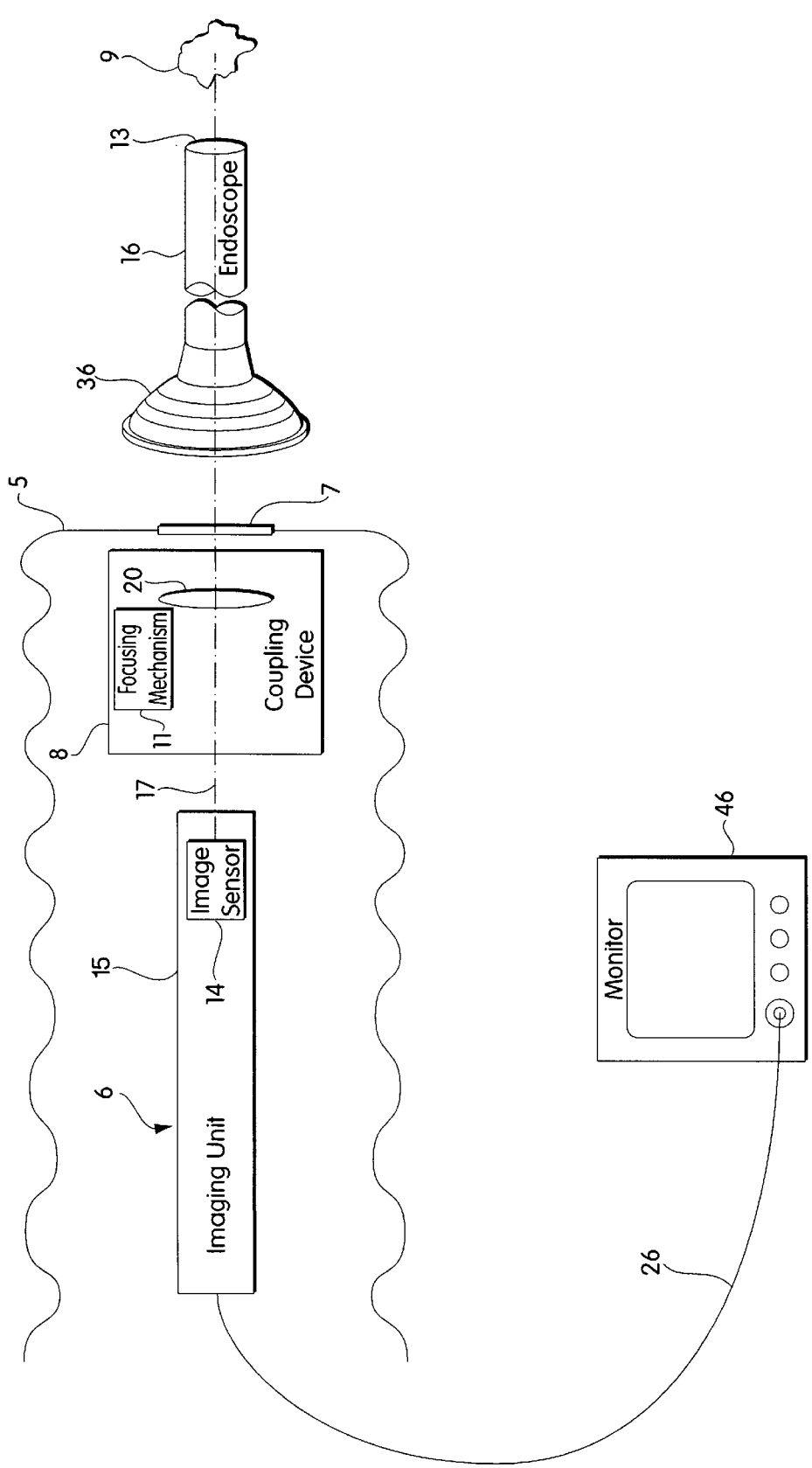
FIG. 1 is a schematic representation of a prior art imaging system that uses a coupling device to interconnect an endoscope and an imaging unit.

Applicant has recognized numerous drawbacks of prior art coupling devices and the imaging systems in which they are used. A brief discussion of two of these drawbacks follows with reference to FIG. 1.

A first drawback is that the portion of the condom-like sheath 5 that intersects the optical axis 17 of the image sensor 14 can interfere with the quality of the image generated on the monitor 46. The condom-like sheath 5 is typically formed of pliable material that can wrinkle in front of lens 20, thereby causing the image generated by image sensor 14 to be distorted. Some prior art systems form the window 7 out of a stiffer material that is less likely to wrinkle. Nevertheless, it can be difficult to properly align the window 7 in front of the lens 20 when sandwiching the sheath 5 between the endoscope 16 and the coupling device 8.

A second drawback is that the sheath 5 is draped over the coupling device 8 and the focusing mechanism 11 located thereon. Thus, the user must manipulate the focusing mechanism 11 through the material of sheath 5. This makes it difficult for the user to precisely adjust the focal length between the image sensor 14 and lens 20 to achieve a sharp image on the monitor 46, and makes the sheath 5 susceptible to tearing due to manipulation of the focusing mechanism.

One exemplary embodiment of the invention discussed below in connection with FIGS. 2–4 overcomes each of the above-mentioned drawbacks. However, it should be appreciated that the present invention is not limited in this respect, and that alternate embodiments of the invention are contemplated that separately overcome either of these drawbacks. Furthermore, it should be understood that the illustrated embodiment of the present invention also has numerous other advantages.

Figure 2:
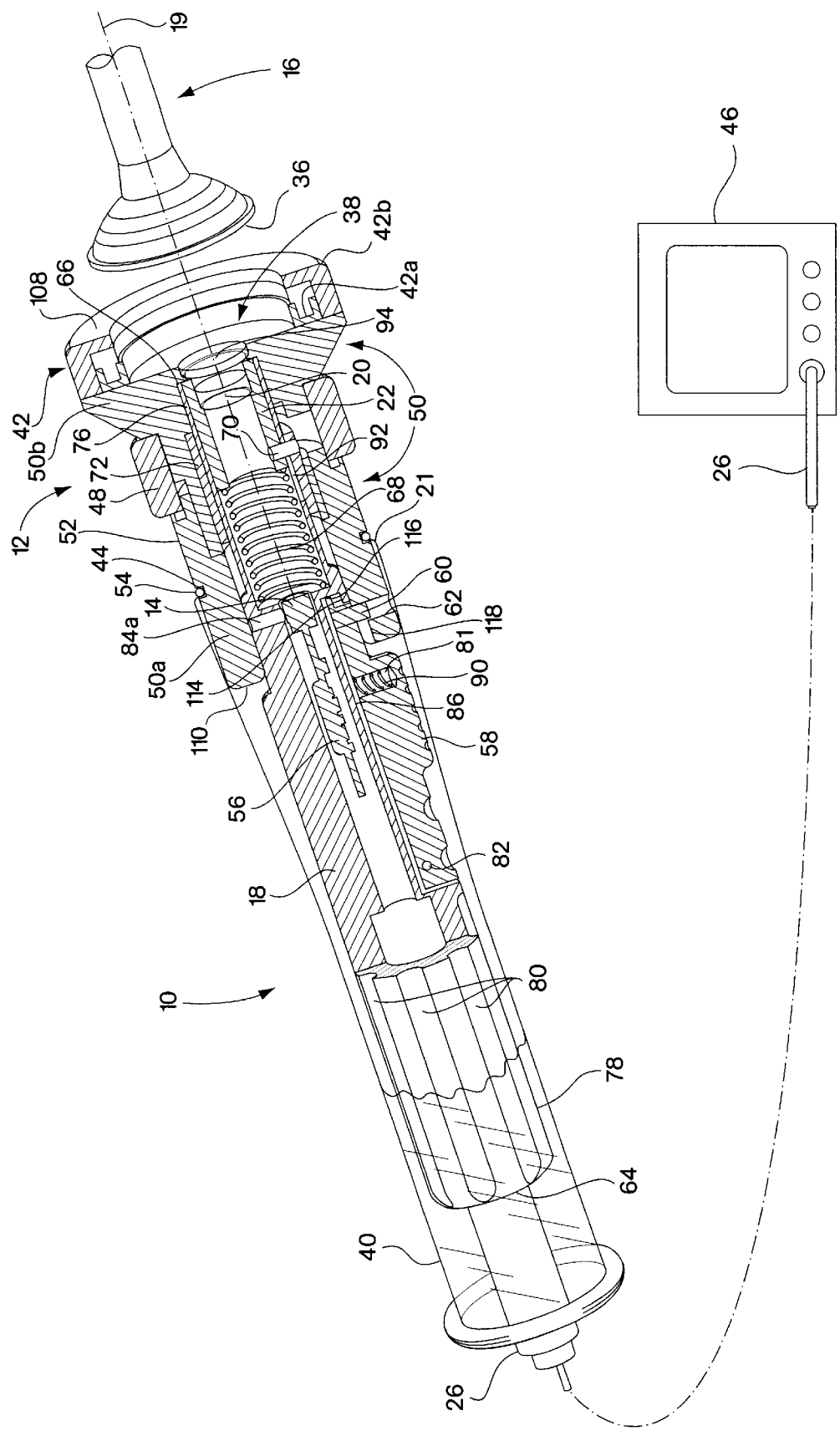
FIG. 2 is a partially cut away perspective view of a coupling device and imaging unit according to one illustrative embodiment of the invention.

FIG. 2 is a partially cut away perspective view of an imaging system according to one embodiment of the invention. As shown, the imaging system includes four primary components, i.e., an endoscope 16, an imaging unit 10, a coupling device 12, which couples the endoscope 16 to the imaging unit 10, and a condom-like sheath 40, which prevents the imaging unit 10 from contaminating the sterile operating field. The imaging system can be employed with any type of image-producing scope, and is not limited to use with any particular type of scope.

As discussed in more detail below, in the exemplary imaging system shown in FIGS. 2–3, the condom-like sheath 40 does not intercept the optical viewing axis of the system, thereby overcoming a number of the problems experienced in the prior art system of FIG. 1. In addition, the condom-like sheath 40 does not cover a focusing mechanism 48 of the imaging system, making it easier to focus the system and lessening the likelihood that the sheath 40 will be damaged due to manipulation of the focusing mechanism.

Figure 3:
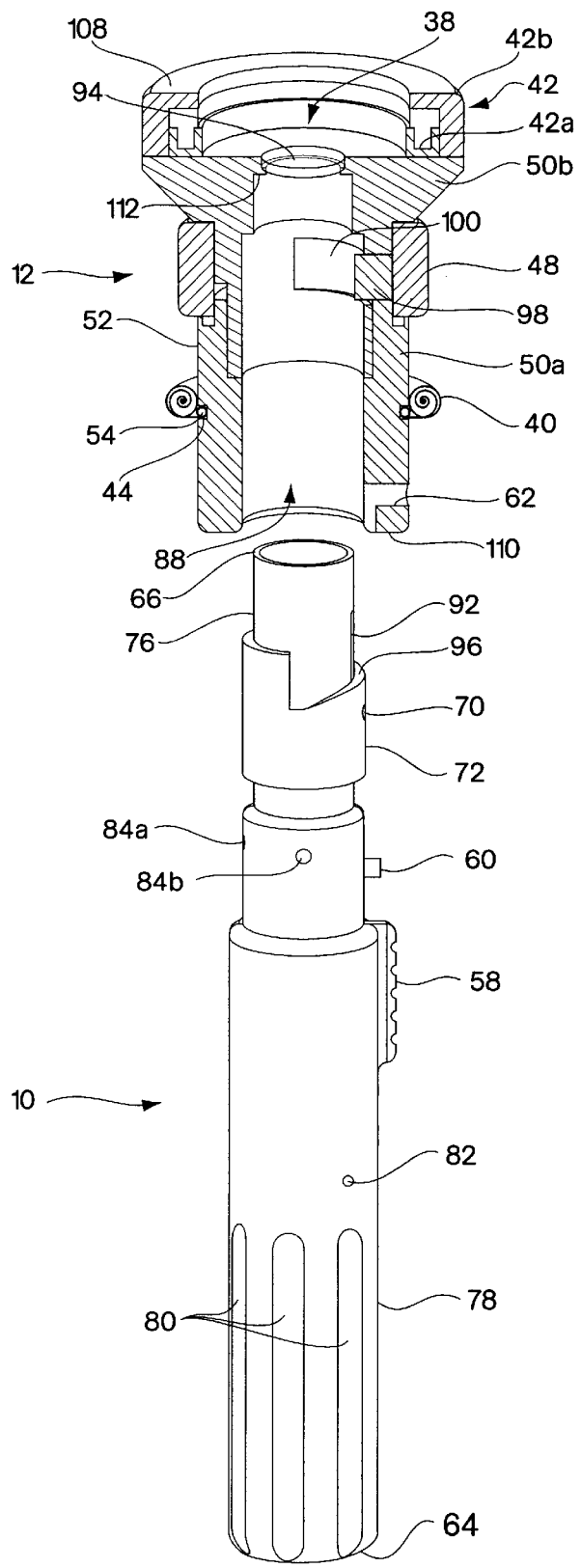
FIG. 3 is a partially cut away perspective view of the coupling device and the imaging unit shown in FIG. 2.

Another significant difference between the embodiment of FIGS. 2–3 and the prior art system of FIG. 1 is that the lens for focusing the image from the endoscope to the imaging unit is provided in the imaging unit 10, rather than in the coupling device 12. This is particularly advantageous because, as discussed in more detail below, in the exemplary embodiment shown, a portion of the coupling device 12 is not separated from the endoscope 16 by the condom-like sheath 40, and therefore, is sterile in use. By removing the focusing lens 20 from the coupling device 12, the coupling device 12 can be made significantly less expensively, thereby enabling the coupling device 12 to be provided as a disposable part that need not be sterilized between uses. This is advantageous because the sterilization of the devices can be inconvenient and time consuming.

In the embodiment shown in FIGS. 2–3, the imaging unit 10 includes an image sensor 14 that is similar to that employed in the prior art system of FIG. 1, and that senses an image along an imaging axis (not shown). As with the prior art system of FIG. 1, when the imaging system is used, the coupling device 12 is coupled between the eyepiece 36 of the endoscope 16 and a distal end 66 of the imaging unit 10 such that the lens 20 is disposed between the image sensor 14 and the eyepiece 36 to focus an image produced by the endoscope 16 onto the image sensor 14. However, in contrast to the prior art system of FIG. 1, the lens 20 is provided in the imaging unit 10, rather than in the coupling device 12. As discussed above, this is advantageous because the coupling device can be made significantly less expensively, thereby enabling the coupling device to be provided as a disposable part that need not be sterilized between uses.

The image sensor 14 may, for example, include a charge-coupled device (CCD) or a metal-oxide semiconductor (MOS) sensor. It should be appreciated, however, that the present invention is not limited in this respect, and can be employed with any type of image sensor 14. The image generated by the image sensor 14 can be conveyed to a monitor 46 in any of numerous ways, and the present invention is not limited to any particular implementation. For example, the image sensor 14 may be coupled to circuitry 56 which can assist in converting an image sensed by the image sensor 14 into an electrical signal. This electrical signal then may be transmitted (e.g., via cable 26) to the monitor 46 for display to a user or may be otherwise processed and/or recorded on a suitable medium. Alternatively, the image sensor 14 may comprise a bundle of fiber optic cables which optically transmit an image from the lens 20 to a viewing device for display to a user. Thus, the image sensor 14 need not necessarily convert the image from endoscope 16 into an electrical signal.

In the embodiment shown in FIG. 2, the imaging unit 10 is releasably mated with the coupling device 12. This mating may be accomplished using any of a number of techniques, and the invention is not limited to any particular mating technique. FIGS. 2 and 3, however, illustrate one technique that may be used to mate these two components. In the particular embodiment shown, to mate imaging unit 10 with coupling device 12, a distal end 66 of the imaging unit 10 is inserted into an opening 88 at a proximal end 110 of the coupling device 12. As shown, the imaging unit 10 includes a button 58 which is pivotally connected, via a pin 82, to a body portion 18 of the imaging unit 10. The imaging unit 10 has a cavity 81 formed underneath the button 58 and a spring 90, disposed in the cavity 81. Spring 90 biases the button 58 (in a clockwise direction in FIG. 2) about pin 82 so that locking member 60 is biased away from a surface 86 of body portion 18. When a user pushes button 58 toward surface 86, however, spring 90 is compressed so that button 58 moves in a counterclockwise direction in FIG. 2 about pin 82 and locking member 60 moves toward surface 86. Thus, when the button 58 is depressed and the distal end 66 of the imaging unit is inserted into the opening 88 in the coupling device 12, the locking member 60 moves toward surface 86 so that it can slide over edge 118 of the coupling device 12. When the button 58 is released, the locking member 60 is biased (by spring 90) away from surface 86 and into a notch 62 in the coupling device 12, and a shoulder 116 of imaging unit 10 contacts a shoulder 114 of the coupling device 12, thereby interlocking the imaging unit 10 and the coupling device 12. An indication that the distal end 66 of the imaging unit 10 is fully inserted into the opening 88 is provided by the distal end 66 contacting a shoulder 112 of coupling device 12. The imaging unit 10 and coupling device 12 can be separated by pushing button 58, which moves the locking member 60 out of the notch 62, and pulling the imaging unit 10 away from the coupling device 12. As mentioned above, FIGS. 2–3 illustrate only one example of the many ways that the imaging unit 10 and coupling device 12 may be mated together, and the present invention is not limited to this or any other particular implementation.

In the embodiment shown in FIGS. 2 and 3, the imaging unit 10 also includes a handle 78 proximal to the body portion 18. The handle 78 may include grooves 80 to make it easier for a user to grip the imaging unit 10 though the sheath 40 that can be extended over the imaging unit 10 in a manner described below.

The image sensor 14 and circuitry 56 may be mounted in the body portion 18 of the imaging unit 10 in any of a number of ways. For example, the image sensor 14 may be mounted via pins or screws 84a and 84b, and circuitry 56 may be mounted on a circuit board supported within body portion 18. One or more wires (not shown) may be used to interconnect the circuitry 56 with the cable 26.

As discussed above, it is useful to enable the focal length between the image sensor 14 and the lens 20 of imaging unit 10 to be adjusted. In accordance with one exemplary embodiment of the invention, this can be accomplished via a mechanism that is not covered by the condom-like sheath 40, thereby making it easier to focus the system and lessening the likelihood that the sheath 40 will be damaged due to manipulation of the focusing mechanism. It should be appreciated, however, that the present invention is not limited in this respect, and that the focal length adjustment can be accomplished in any number of ways.

One example of a technique that is useful to perform the focal length adjustment is illustrated in FIGS. 2–4. In the embodiment shown, the lens 20 is disposed in the imaging unit 10, rather than in the coupling device 12. Thus, the focusing mechanism includes elements disposed in the imaging unit 10, as well as in the coupling device 12. As mentioned above, placement of the lens 20 within the imaging unit 10, rather than in the coupling device 12, provides at least one significant advantage. That is, according to such an embodiment, the cost of the coupling device 12 may be reduced significantly below the cost of coupling devices that include lenses, thereby making it commercially practicable to use a new, sterile coupling device each time the imaging system is used, rather than repeatedly sterilizing and reusing the same coupling device.

In the particular embodiment shown, the distal end 66 of the imaging unit 10 includes a primary cylinder 76, in which a spring 68 and a cylindrical lens holder 22 are disposed. Lens holder 22 supports the lens 20 in front of an imaging axis of image sensor 14. Lens holder 22 (and lens 20) can be moved within primary cylinder 76 either toward or away from distal end 66 of the imaging unit 10 so as to adjust the focal length between the image sensor 14 and the lens 20. Spring 68 biases lens holder 22 toward distal end 66. The position of lens holder 22 within primary cylinder 76 can be adjusted, however, through manipulation of a focusing mechanism on the coupling device 12 as discussed below.

The imaging unit 10 further includes an outer cylinder 72, including a spirally ramped upper edge 96, which surrounds the primary cylinder 76. Outer cylinder 72 is movable with respect to primary cylinder 76 either toward or away from the distal end 66 of imaging unit 10. Outer cylinder 72 is connected to the lens holder 22 via a pin 70. Pin 70 extends through a slot 92 which extends a short distance along a length of the primary cylinder 76. Thus, in the embodiment shown, lens holder 22, outer cylinder 72 and pin 70 move as a single unit, with respect to primary cylinder 76, either toward or away from the distal end 66 of imaging unit 10. The manner in which this unit interacts with the focusing mechanism disposed on coupling device 12 is described below in connection with FIGS. 4a–b.

FIGS. 2 and 3 show an exemplary embodiment of the coupling device 12. The coupling device 12 can be constructed in any of a number of ways to achieve the desired goal of enabling the imaging unit 10 to be coupled to the endoscope 16, and the present invention is not limited to the particular implementation shown in the figures. In the embodiment shown, the coupling device 12 includes a main body 50 (including a proximal portion 50a and a distal portion 50b), a focusing ring 48, a light-penetrable window 94, a scope mounting portion 42 (including inner ring 42a and outer ring 42b) and the condom-like sheath 40. The components constituting the main body 50, focusing ring 48 and scope-mounting portion 42 may be made of any suitable material and may be affixed together in any suitable manner. For example, they may be plastic molded components affixed together using an epoxy-based adhesive. For the embodiment of the invention wherein the coupling device 12 is a disposable device, the coupling device 12 is preferably formed from inexpensive components.

The main body 50 may be formed by inserting the distal portion 50b within the focusing ring 48, and then affixing together the proximal and distal portions 50a and 50b. Scope mounting portion 42 may be affixed to distal portion 50b. Main body 50 has an outer surface 52 between a distal end 108 and a proximal end 10 of the coupling device 12. A channel 44 extends about a perimeter of the outer surface 52 between the focusing ring 48 and the proximal end 110.

When the coupling device 12 is used in a medical application, it is generally important that the environment to which the patient is exposed remains sterile. It is also desirable, however, to not have to sterilize the imaging unit 10, thereby saving the time and expense of sterilization, and avoiding restrictions on the manner in which the imaging unit be formed, since it need not be sterilizable. Therefore, in accordance with one embodiment of the present invention, a sterile barrier is established between the sterile operating environment including the endoscope 16, and a non-sterile environment including the imaging unit 10. In one embodiment of the invention, such a sterile barrier is established by coupling the distal end 66 of the imaging unit 10 to the coupling device 12, and providing a hermetic seal between the components of the coupling device 12 that separate the sterile and non-sterile environments. In the embodiment shown in the figures, a light-penetrable window 94 is hermetically sealed between the distal end 108 and the proximal end 110 of the coupling device 12 to establish a sterile barrier therebetween. Window 94 may be made of glass, plastic, or any other suitable material through which light can pass from the endoscope 16 to the image sensor 14 (via lens 20) to generate a suitable image.

As mentioned above, the coupling device 12 also includes the condom-like sheath 40. The condom-like sheath 40 may be made of any material that is suitable for creating a sterile barrier between a sterile environment and a non-sterile environment. For example, according to one embodiment, the condom-like sheath may be made of a non-porous latex or plastic material. When the imaging unit 10 is mated with the coupling device 12, the sheath 40 may be extended to cover some or all of imaging unit 10 and cable 26 (FIG. 2). The condom-like sheath 40 may be hermetically sealed to the outer surface 52 of coupling device 12. It should be appreciated that in the embodiment shown in the figures, when each of the components of the coupling device 12 is sterile, the hermetic seals between the main body portion 50 and the window 94 and sheath 40 establish a sterile barrier between the endoscope 16 and the imaging unit 10, with the main body portion 50 of the coupling device 12 itself forming a part of this sterile barrier. As compared to the prior art system shown in FIG. 1, in which a sterile barrier is formed only with the sheath 5 and the window portion 7 thereof and in which the coupling device 8 is located entirely on the non-sterile side of this barrier, the embodiment shown in FIGS. 2–3 is superior because endoscope 16 can mate directly with body portion 50 rather than requiring the sheath to be interposed between the coupling device and the endoscope as was done in the prior art. This feature therefore overcomes the drawbacks of the prior art system described above regarding the impact of the sheath of the quality of the image produced by the system, and the difficulty of properly sandwiching the sheath between the coupling device and the endoscope.

According to one embodiment of the present invention, the condom-like sheath 40 does not intercept the optical viewing axis 19 of the imaging system. As mentioned above, this is advantageous in that the sheath 40 need not be provided with a window that must be aligned with the optical viewing axis 19, and the sheath 40 does not interfere with the quality of the image presented on the monitor 46. It should be appreciated that the function performed by the condom-like sheath 40 can be achieved in any of numerous ways, and that the present invention is not limited to any particular implementation. For example, a protective sheath can be provided that is more rigid than the condom-like sheath 40 depicted in the drawings In the embodiment shown in the drawings, the condom-like sheath 40 is substantially tubular in form and is open on its distal and proximal ends. The distal end 21 of the condom-like sheath 40 is attached to the outer surface 52 (within channel 44) of the coupling device 12. As discussed above, in one embodiment of the present invention, this attachment can be accomplished using a hermetic seal (e.g., via an O-ring 54) to maintain the separation between the sterile and non-sterile environments. The condom-like sheath 40 can be provided in a rolled-up form attached to the coupling device 12. After the coupling device 12 is mated with to the imaging unit 10 as described above, the condom-like sheath 40 can be unrolled to cover the non-sterile imaging unit 10. By encompassing the outer surface 52 of coupling device 12 with the opening at the distal end 21 of the sheath 40, the sheath 40 can be used in conjunction with coupling device 12 without requiring the user to align the sheath 40, or a window portion thereof, between the eyepiece 36 of the endoscope 16 and the coupling device 12, and without having the sheath 40 intercept the optical viewing axis 19 of the imaging system.

FIGS. 2 and 3 illustrate one example of a technique that may be used to mate the endoscope 16 with the coupling device 12. It should be appreciated that the invention is not limited in this respect, and that numerous other suitable mating techniques can be employed. In the embodiment shown in FIGS. 2 and 3, the endoscope 16 is mated with the coupling device 12 by inserting the eyepiece 36 into an opening 38 at the distal end 108 of the coupling device 12. Opening 38 may be formed by the inner and outer rings 42a–b of the scope mounting portion 42. In the embodiment shown, the inner and outer rings 42a–b form equal diameter openings, and inner ring 42a is movable with respect to outer ring 42b. A spring biases the inner ring 42a so that its center is forced to be offset from the center of the outer ring 42b unless a user activates a lever (not shown) to cause the centers of the two rings to align with one another.

To mate the endoscope 16 with the coupling device 12, the user activates the lever so that the centers of the rings 42a–b align with one another and inserts the eyepiece 36 through both rings. The user then can release the lever so that the spring (not shown) causes the center of ring 42a to become offset from the center of ring 42b. Because the diameter of the eyepiece 36 is only slightly smaller than the diameter of each of rings 42a and 42b, when the centers of the rings are offset from one another, the eyepiece 36 will be locked within the scope mounting portion 42 of the coupling device 12. The eyepiece 36 may be separated from the scope mounting portion 42 by pressing the lever to realign the centers of rings 42a and 42b and pulling the endoscope 16 away from the coupling device 12.

As discussed above, according to one embodiment of the invention, the user can directly manipulate a focusing mechanism without having to do so through a portion of a protective sheath such as condom-like sheath 40. The present invention is not limited to use with any particular type of focusing mechanism, as any mechanism can be employed that serves to adjust the focal length between the lens 20 and image sensor 14 in the imaging unit 10. In the exemplary embodiment of the invention shown in FIGS. 2–4, a focusing ring 48 is provided on the coupling device 12 to perform this focal length adjustment. The focusing ring 48 is disposed distally of the distal end 21 of the condom-like sheath 40, so that after the sheath 40 is extended to cover some or all of the imaging unit 10 and cable 26 (FIG. 2), the focusing ring 48 is not covered by the sheath 40 and may be manipulated by a user to adjust the focal length between the lens 20 and the image sensor 14 without also having to manipulate the sheath 40. Hence, this feature makes focusing ring 48 relatively easy for the user to manipulate to achieve sharp focusing, and reduces the risk of damage to sheath 40.

Figure 4A:
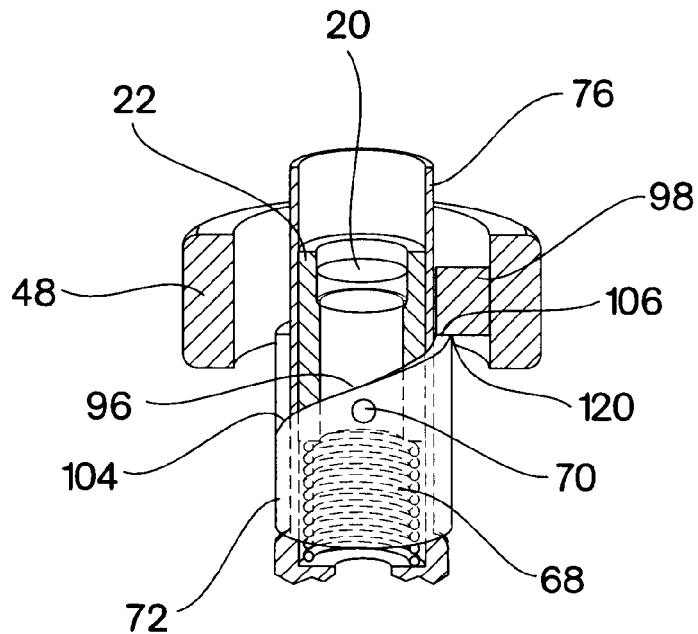
FIGS. 4a and 4b are partially cut away perspective views of an illustrative focusing mechanism employed in the system of FIGS. 2 and 3.
Figure 4B:
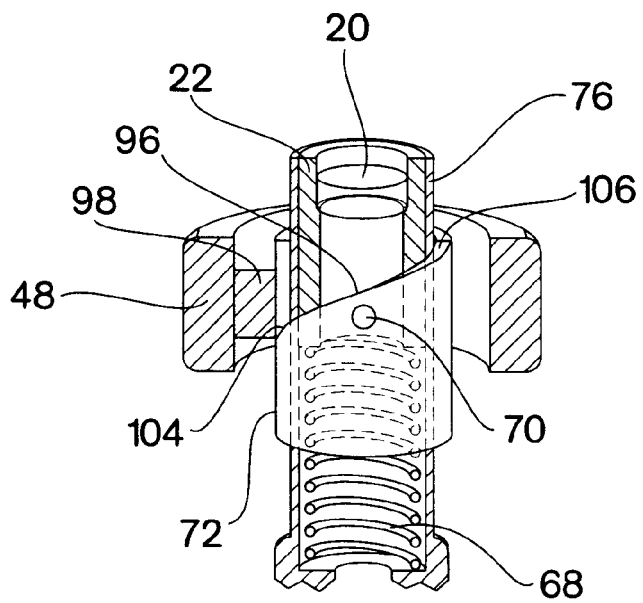

An illustrative example of a linkage assembly for mechanically coupling the focusing ring 48 on the coupling device 12 to the imaging unit 10 to adjust the focal length between the lens 20 and image sensor 14 is shown in FIGS. 3 and 4a–b. It should be appreciated that the present invention is not limited to this particular linkage assembly, as numerous other implementations are possible. In the embodiment shown, the distal portion 50b of the main body portion 50 of coupling device 12 has an annular groove 100. Annular groove 100 may be covered by the focusing ring 48, so that it is not visible from the outside of coupling device 12. A finger 98 extends inwardly from the focusing ring 48 through the annular groove 100, so that when the focusing ring 48 is rotated about the main body portion 50, finger 98 slides within the annular groove 100.

As shown in FIGS. 4a–b, when the imaging unit 10 is mated with the coupling device 12, a lower surface 120 of finger 98 contacts a portion of a spiraling ramp surface 96 on the outer cylinder 72. As mentioned above, pin 70 may be connected between the outer cylinder 72 and the cylindrical lens holder 22 through the slot 92, which extends along the length of the primary cylinder 76, so that the outer cylinder 72 and lens holder 22 do not rotate with respect to the primary cylinder 76. The focusing ring 48, however, can rotate freely about the primary cylinder 76, limited only by the movement of the finger 98 within the annular groove 100.

As the focusing ring 48 rotates with respect to the primary cylinder 76, a bottom surface 120 of the finger 98 slides along the spiraling ramped surface 96. The spring 68 pushes upwardly on outer cylinder 72 to keep a portion of the spiraling ramped upper surface 96 in contact with bottom surface 120 of the finger 98 at all times. Enough friction exists between the focusing ring 48 and the main body 50 of the coupling device 12 to prevent the spring 68 from rotating the focusing ring 48 when it is not being manipulated by a user. This friction makes the fine tuning of the focal length between the lens 20 and image sensor 14 (using focusing ring 48) relatively easy to accomplish.

FIGS. 4a and 4b illustrate the focusing mechanism at its two extreme focusing positions, with FIG. 4a illustrating the lens 20 at its closest position to the image sensor 14 and FIG. 4b illustrating the lens 20 at its furthest position from the image sensor 14. As shown in FIG. 4a, when the lens 20 is at its closest position to the image sensor 14, the spring 68 is fully compressed, bottom surface 120 of finger 98 is in contact with a point 106 near the top of the spiraling ramped surface 96, and the finger 98 is in a first position with respect to the primary cylinder 76. In contrast, as shown in FIG. 4b, when the lens 20 is at its furthest position from the image sensor 14, the spring 68 is fully extended, the bottom surface 120 of finger 98 is in contact with a point 104 near the bottom of the spiraling ramped surface 96, and the finger 98 is in a second position with respect to the primary cylinder 76, which is on an opposite side from the first position (FIG. 4a).

It should be appreciated that the present invention is not limited to the above-described system for adjusting the focal length between the image sensor 14 and the lens 20. This implementation is only one example of the many possible systems that can achieve this result, as other implementations can alternatively be employed.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. An apparatus for mating a scope with an imaging instrument which includes an image sensor to receive, along an optical axis, an image produced by the scope, the apparatus comprising:

a coupler having first and second ends, the first end being adapted to mate with the scope, the second end being adapted to mate with the imaging instrument, the coupler defining a light-transmissive passage between the first and second ends so that the image produced by the scope can be transmitted through the light-transmissive passage to the image sensor; and a focusing mechanism disposed on the coupler such that, when the coupler is mated with the imaging instrument and the scope, adjustment of the focusing mechanism causes a position of a refractive lens intercepted by the optical axis and included in a device other than the coupler to be adjusted to focus the image produced by the scope onto the image sensor.

2. The apparatus as claimed in claim 1, further comprising a light-penetrable window positioned in the passage and hermetically sealed between the first and second ends of the coupler.

3. The apparatus as claimed in claim 1, wherein the refractive lens is included in the imaging instrument, and wherein the focusing mechanism is adapted to adjust a focal length between the lens and the image sensor.

4. The apparatus as claimed in claim 3, in combination with the imaging instrument.

5. The apparatus as claimed in claim 1, further including a sterile sheath hermetically sealed to the coupler.

6. The apparatus as claimed in claim 5, wherein the coupler is sterile distally of a distal end of the sterile sheath.

7. The apparatus as claimed in claim 1, wherein the coupler is disposable.

8. The apparatus as claimed in claim 1, wherein the first and second ends of the coupler are respectively adapted to releasably mate with the scope and the imaging instrument.

9. The apparatus as claimed in claim 8, wherein:

the scope includes an eyepiece, and the first end of the coupler is adapted to releasably mate with the eyepiece of the scope.

10. The apparatus as claimed in claim 1, wherein:

the scope includes an eyepiece, and the first end of the coupler is adapted to mate with the eyepiece of the scope.

11. The apparatus as claimed in claim 1, wherein the light-transmissive passage is free of a refractive lens that intercepts the optical axis.

12. The apparatus as claimed in claim 1, wherein the apparatus further includes a sterile sheath disposed on the coupler and wherein the sterile sheath is extendable to accommodate at least a portion of the imaging instrument when the imaging instrument is mated with the second end of the coupler.

13. The apparatus as claimed in claim 12, wherein the coupler has an outer surface, and wherein the sterile sheath has an opening mounted about the outer surface of the coupler.

14. The apparatus as claimed in claim 12, wherein the focusing mechanism is disposed distally of a distal end of the sterile sheath.

15. A coupler for coupling a scope with an imaging instrument including an image sensor to receive, along an optical axis, an image produced by the scope, the imaging instrument including a refractive lens to intercept the optical axis between the scope and the image sensor, the coupler comprising:

a body having a first end adapted to mate with the scope and a second end adapted to mate with the imaging instrument; and a focusing mechanism disposed on the body and adapted to focus the refractive lens within the imaging instrument.

16. The apparatus as claimed in claim 15, wherein the coupler further includes a sterile sheath which is extendable to accommodate at least a portion of the imaging instrument when the imaging instrument is mated with the second end of the body.

17. The apparatus as claimed in claim 16, wherein the body has an outer surface, and wherein the sterile sheath has an opening mounted about the outer surface of the body.

18. The apparatus as claimed in claim 15, wherein the focusing mechanism is disposed distally of a distal end of the sterile sheath.

19. The apparatus as claimed in claim 16, wherein the body is sterile distally of a distal end of the sterile sheath.

20. The apparatus as claimed in claim 16, wherein the sterile sheath is hermetically sealed to the body.

21. The apparatus as claimed in claim 15, wherein the body defines a passage between the first and second ends of the body that is adapted to be in-line with the optical axis, so that the image produced by the scope can be transmitted through the passage to the image sensor.

22. The apparatus as claimed in claim 21, further comprising a light-penetrable window positioned in the passage and hermetically sealed between the first and second ends of the body.

23. The apparatus as claimed in claim 21, wherein the first and second ends of the body are respectively adapted to releasably mate with the scope and the imaging instrument.

24. The apparatus as claimed in claim 15, in combination with the imaging instrument.

25. The apparatus as claimed in claim 15, wherein the coupler is disposable.

26. The apparatus as claimed in claim 15, wherein the first and second ends of the coupler are respectively adapted to releasably mate with the scope and the imaging instrument.

27. The apparatus as claimed in claim 26, wherein:

the scope includes an eyepiece, and the first end of the body is adapted to releasably mate with the eyepiece of the scope.

28. The apparatus as claimed in claim 15, wherein:

the scope includes an eyepiece, and the first end of the body is adapted to mate with the eyepiece of the scope.

* * * * *